(12) United States Patent
Chuck (10) Patent No.: US 7,749,726 B2
(45) Date of Patent: Jul. 6, 2010

(54) METHODS FOR IDENTIFYING AND ISOLATING STEM CELLS

(76) Inventor: Roy S. Chuck, 7105 Charles Spring Way, Towson, MD (US) 21024

( * ) Notice: Subject to any disclaimer, the term of this patent is extended or adjusted under 35 U.S.C. 154(b) by 119 days.

(21) Appl. No.: 11/667,280

(22) PCT Filed: Nov. 8, 2005

(86) PCT No.: PCT/US2005/040406

§ 371 (c)(1),
(2), (4) Date: Nov. 1, 2007

(87) PCT Pub. No.: WO2006/055338

PCT Pub. Date: May 26, 2006

(65) Prior Publication Data

US 2008/0193929 A1    Aug. 14, 2008

Related U.S. Application Data

(60) Provisional application No. 60/625,597, filed on Nov. 8, 2004.

(51) Int. Cl.
*C12Q 1/02* (2006.01)

(52) U.S. Cl. .......................... 435/29; 435/325; 435/366; 435/377

(58) Field of Classification Search .................. 435/29, 435/325, 366, 377
See application file for complete search history.

(56) References Cited

U.S. PATENT DOCUMENTS

| 4,162,405 | A | 7/1979 | Chance et al. |
|---|---|---|---|
| 4,354,114 | A | 10/1982 | Karnaukhov et al. |
| 2005/0036667 | A1 | 2/2005 | So et al. |
| 2008/0090266 | A1 * | 4/2008 | Hattori et al. .................. 435/29 |
| 2009/0093807 | A1 * | 4/2009 | Hyde et al. .................... 606/34 |

OTHER PUBLICATIONS

Huang, et al., Two Photon Fluorescence Spectroscopy and Microscopy of NAD(P)H and Flavoprotein, Biophysical Journal May 2002, vol. 82, No. 5, pp. 2811-2825.

* cited by examiner

*Primary Examiner*—Ralph Gitomer
(74) *Attorney, Agent, or Firm*—Robert D. Buyan; Stout, Uxa, Buyan & Mullins (57) ABSTRACT

Methods and systems for a) identifying and isolating stem cells, b) assessing mitochondrial distribution and structure in living cells and c) performing fluorescence microscopy on living cells while the cells remain within a condition-controlled cell culture chamber.

24 Claims, 4 Drawing Sheets

METHODS FOR IDENTIFYING AND ISOLATING STEM CELLS

RELATED APPLICATION

This utility patent application claims priority to U.S. Provisional Patent Application No. 60/625,597 filed on Nov. 8, 2004, the entirety of which is expressly incorporated herein by reference.

STATEMENT REGARDING GOVERNMENT SUPPORT

Aspects of this invention were made with government support through National Institutes of Health grant number EY000412-04. Accordingly, the government may have certain rights in this invention.

FIELD OF THE INVENTION

This invention relates broadly to the fields of biology and medicine and more specifically to methods and systems for identifying and isolating stem cells, assessing mitochondrial distribution and structure in living cells and performing fluorescence microscopy on living cells while the cells remain within a condition-controlled cell culture chamber.

BACKGROUND OF THE INVENTION

Stem Cells

Stem cells are undifferentiated primal cells that are capable of differentiating into cells of various other types. Because of their ability to form various types of differentiated cells, stem cells function to replenish other cells throughout the life of the organism.

Research efforts are currently aimed at developing methods wherein stem cells are used to repair damaged tissues or to grow replacement organs or body parts. In order for stem cells to be routinely useable for such therapeutic applications, it will be necessary to develop techniques for efficiently and reliably identifying and isolating stem cells from populations of other differentiated cells.

Stem Cell Identification and Isolation

Techniques to isolate adult and embryonic stem cells for clinical and experimental use are in development by many workers. However, although much effort has been expended in searching for stem cell probes, currently there still exists no reliably specific marker for stem cells of any type. Additionally, many of the markers that have been proposed and studied are invasive to the cell or cell surface and may alter or even kill the cell.

One of the most accepted properties of stem cells is their ability to slowly cycle and continuously replenish cell populations. We hypothesized and found that such slow cycling cells can be characterized by slower intrinsic metabolism. As such, these slow cycling populations are detectable via metabolic monitoring. We have developed a novel fluorescence spectroscopic technique and device to separate live, unlabeled stem cells from further differentiated stages of development based on this simple finding.

Currently there exists no reliable, non-invasive technique to specifically detect or screen for the presence of stem cells, or to reliably isolate stem cells from a matrix that contains stem cells along with other types of cells. Development of such a technique, especially a generalizable one, would not only represent a unique stem cell detection and separation method/device, but would also provide a viable alternative to the currently popular search for lineage-specific markers.

Mitochondria

Mitochondria are elongate or rod shaped, membrane-enclosed, organelles located within cells of the body. Mitochondria function as the major source of a cell's energy by oxidizing the products of carbohydrate and lipid metabolism. Mitochondria are located outside the nucleus of the cell but contain some independent DNA and may be reproduced as needed by the cell within which they reside. Damage to mitochondria can result in muscular weakness and fatigue and, in some cases, may lead to life-threatening conditions, such as lactic acidosis. Nucleoside analogs may cause mitochondrial toxicity.

In normal healthy cells, mitochondria are diffusely distributed throughout the cytoplasm. Abnormal clustering of mitochondria in the perinuclear region of the cell can be indicative of changes in the metabolic state of the cell. Existing literature supports two mechanisms to explain how mitochondrial redistribution occurs. Firstly, these organelles may simply migrate via a complex microtubular network from the perinuclear region to the cell periphery. In cells transfected with a mutant member of dynamin, a family of membrane transport proteins, perinuclear aggregates of mitochondria were demonstrated by electron microscopy, whereas cells with normal tubular projections exhibited diffuse mitochondrial arrangement. Impairment of kinesin-mediated transport by tumor necrosis factor-related apoptosis inducing ligand (TRAIL) also leads to these changes in mitochondrial distribution. Furthermore, treatment with microtubule-active drugs (taxol, nocodazole and colchicine) results in perinuclear clustering of mitochondria. The second mechanism involves the presence of two populations of mitochondria, perinuclear and peripheral, as observed by confocal fluorescence microscopy of mitochondria labeled with two potentiometric probes, rhodamine 123 and dimethylaminostyrylmethylpyridiniumiodine, with each population exhibiting different levels of activity and morphology depending on cell type. Cultured cancer cells have exhibited increased perinuclear fluorescence in strains sensitive to chemotherapeutic drugs and increased peripheral activity and consequently fluorescence, in the mitochondria of resistant strains.

There exists a need for the development of new techniques for assessing changes or abnormalities of mitochondrial distribution and structure in living cells without the need for killing the cell or destroying the tissue within which the cell is located.

Reduction-oxidation (Redox) Fluorometry

Redox Fluorometry is an optical spectroscopic technique wherein autofluorescence is measured from reduced pyridine nucleotides (PN) and oxidized flavoproteins (Fp). The ratio of PN to Fp (PN/Fp ratio) is then calculated. This PN/Fp ratio may be used as an indicator of tissue metabolic rate.

In the performance of redox fluorometry, the amount of PN (i.e., NADH and NADPH) may be estimated by detecting fluorescence emission in the region of 450 nm after excitation at 366 nm. This estimate includes both cytoplasmic and mitochondrial NADH and NADPH, with greater quantum yield from the mitochondrial bound species. The amount of Fp (i.e., lipoamide dehydrogenase (LipDH) and electron transfer flavoprotein (ETF)) is then estimated by detection of fluorescence in the region of 540 nm after excitation at 460 nm. This measures cellular levels of the flavoproteins which exist mostly as co-factors for enzymes involved in redox reactions. The ratio of these fluorescence measurements, which minimizes interfering factors such as absorption of excitation and emission light by other intrinsic chromophores, light scattering, and variations in mitochondrial density and flavoprotein concentration, has previously been proposed as a non-invasive measure of the organ cellular metabolic state.

Initially, most redox fluorometry methods were performed using one-photon (1P) excitation at near-UV and visible wavelengths for NAD(P)H and FP fluorescence. However, the use of 1P-redox fluorometry to determine PN/Fp ratios of cells in situ was found to be problematic due to photobleaching of intrinsic fluorophores and other light-induced damage as well as light scattering and absorption in turbid cell and tissue environments. These problems with 1P-redox fluorometry were largely overcome by the use of multiphoton microscopy coupled with near-infrared (NIR) excitation. MPM offers several advantages including a) little or no photobleaching while out of focus, b) three-dimensional resolution, c) less light scattering and photodamage and the ability to determine PN/Fp ratio in tissue planes that are below the surface of an organ or tissue mass. Thus, two-photon (2P) NAD(P)H fluorescence has become a preferred method for performing redox fluorometry of in vivo tissues and some other applications. More recently, the development of two-photon (2P) femtosecond laser excitation and scanning confocal microscopy has enabled the three-dimensional mapping of cellular metabolic oxidation/reduction states in situ with high resolution.

Redox fluorometry has also been applied to the detection of cells with deregulated proliferative potential. Using this noninvasive spectroscopic technique, normal and transformed fibroblasts have been separated, as have proliferating and non-proliferating epithelial cells. More recently others have discovered that intracellular redox state appears to be a necessary and sufficient modulator of the balance between self-renewal and differentiation in dividing optic nerve oligodendrocyte-type-2 astrocyte progenitor cells. That is, the intracellular redox state of freshly isolated progenitors allows prospective isolation of cells with different self-renewal characteristics.

The non-invasive microscopic technique of redox fluorometry, which is based upon stimulated auto fluorescence detection, has been historically suggested as a viable clinical measure of the cellular metabolic state. More recently, redox fluorometry has also been demonstrated to be able to differentiate between self-renewing and differentiating cells.

SUMMARY OF THE INVENTION

The present invention provides a method and system for identifying the presence of stem cells in a sample that contains differentiated cells of a known cell type, such method comprising the steps of (a) measuring the PN/Fp ratio of cells present in the sample and (b) determining whether cells present in the sample exhibit a PN/Fp ratio that is lower than the PN/Fp ratio that is known or expected for differentiated cells of the type present in the sample or within the range of that expected for stem cells of the type potentially present in the sample. Step (a) may be performed by i) determining a first fluorescence emission value indicative of cellular components from reduced pyridine nucleoides, ii) determining a second fluorescence emission value indicative of cellular levels of the flavoproteins lipoamide dehydrogenase (LipDH) and electron transfer flavoprotein (ETF) and iii) determining the ratio of the first fluorescence emission value to the second fluorescence emission value. The first fluorescence emission value may be determined by measurement of fluorescence in the region of 450 nm after excitation at 366 nm. The second fluorescence emission value may be determined by measurement of fluorescence detected in the region of 540 nm after excitation at 460 nm. Thereafter, Step (b) may be performed by first ascertaining either a known or expected PN/Fp ratio for differentiated cells of the type present in the sample and/or ascertaining a known or expected PN/Fp ratio for stem cells of a type potentially present within the sample. The actual PN/Fp ratio(s) measured in Step (a) are compared to the known or expected PN/Fp ratio(s) for differentiated and/or stem cells and, on that basis, a qualitative or quantitative determination is made as to whether the sample contains stem cells.

Further in accordance with the present invention, to facilitate the comparison of the measured PN/Fp ratio(s) to the known or expected PN/Fp ratio(s), the present invention may optionally comprise a database (e.g., an electronically accessible database, look-up table, visual key, etc.) that contains known or expected PN/Fp ratios for various types of human or animal differentiated cells and/or various types of stem cells. Such database may then be used for comparison to the measured PN/Fp ratios to determine whether stem cells are present in the sample.

Still further in accordance with the invention, in some embodiments the sample may comprise cells in a liquid matrix (e.g., cell culture medium, umbilical chord blood, etc.) while in other embodiments the sample may comprise an organ or other mass of solid tissue. In cases where the sample comprises cells in a liquid matrix, one-photon (1P) excitation at near-UV and visible wavelengths may be used for NAD(P)H and FP fluorescence. In cases where the sample comprises an organ or other mass of solid tissue two-photon (2P) NAD(P)H fluorescence may be employed to enable the determination of PN/Fp ratio(s) for cells in vivo, especially for cells located in tissue planes below the surface of the organ or tissue mass. Irrespective of whether the sample comprises cells in a liquid matrix or a solid tissue, the methods of the present invention may be performed on living cells, without requiring the cells to be killed or stained for performance of the method.

Still further in accordance with the present invention, a method and system of the above-summarized character may optionally include the additional step of (c) counting, isolating, sorting or separating stem cells determined to be present within the sample. This optional step may be accomplished by selectively counting, isolating, sorting or separating cells that exhibit a PN/Fp ratio lower than that typical of differentiated cells of the type present in the sample (or those that match an expected PN/Fp ratio for stem cells). This may be accomplished by any suitable means, including but not limited to the use of a fluorescence activated cell sorter (FACS). Examples of commercially available FACS devices that may be useable to practice this method of the present invention include the BD FACSAria™, BD FACSVantage™ and BD FACSCalibur™ available from BD Biosciences, Inc., 2350 Qume Drive, San Jose, Calif., USA 95131-1807 and the ALTRA Cell Sorting System available from Beckman Coulter, Inc., 4300 N. Harbor Boulevard, P.O. Box 3100, Fullerton, Calif. 92834-3100 USA.

Still further in accordance with the present invention, the sample used in the above-summarized methods may comprise cells in a liquid substrate or a solid tissue (e.g., an organ). In instances where the sample comprises solid tissue, it may be difficult to measure the PN/Fp ratio(s) in vivo or in cells located beneath the surface of the tissue using standard one-photon (1P) excitation at near-UV and visible wavelengths for NAD(P)H and FP fluorescence. Thus, in such instances, the present invention may utilize two-photon (2P) NAD(P)H fluorescence to enable measurement of cells located beneath the surface of the tissue or in specific deep tissue planes.

Detailed descriptions of such two-photon (2P) NAD(P)H fluorescence methods are described in the literature. See, Yeh A T, Nassif N, Zoumi A, Tromberg B J.; *Selective Corneal Imaging Using Combined Second-Harmonic Generation And Two-Photon Excited Fluorescence*; Optics Letters 27:2082-4 (2002); Zoumi A, Yeh A, Tromberg B J.; *Imaging Cells And Extracellular Matrix In Vivo By Using Second-Harmonic Generation And Two-Photon Excited Fluorescence*; Proc. Natl. Acad. Sci. USA 99:11014-9 (2002).

Still further in accordance with the present invention, there are provided methods for preparing stem cell isolates and/or preparations for clinical and experimental applications by identifying and isolating stem cells by way of the above-summarized methods of the present invention and subsequently expanding (e.g., culturing) the population of such stem cells if necessary and/or combing the stem cells with other materials or apparatus if necessary, to thereby provide a stem-cell-comprising preparation or article for clinical or research use. Examples of such stem-cell-comprising preparations or articles include but are not limited to: stem cells for subsequent culture and expansion; frozen or otherwise preserved stem cell isolates obtained from an individual's umbilical chord blood, bone marrow or other source(s) for possible use in future stem-cell based therapies of that individual; stem cells for implantation or transplantation into specific organs or tissues for therapeutic purposes (e.g., limbal stem cells for transplantation into or onto an eye to facilitate regeneration of corneal surface epithelium; stem cell preparations for implantation on or near the retina of an eye for treatment of retinal disorders such as retinal degenerations and macular degeneration; stem cell preparations for direct injection into organs of interest (e.g. stem cell preparations for implantation into cardiac tissue for the treatment of cardiac disorders such as ischemia and arrhythmia and or regeneration of new myocardial tissue to replace infracted or necrotic tissue; stem cell preparations for implantation into areas of the brain to give rise to new functional cells such as dopamine secreting cells for the treatment of Parkinsons disease; stem cell preparations for infusion into the blood to give rise to new healthy blood cells and stem cells disposed on substrates, scaffolds, forms, casts or other articles for the formation of prosthetic or replacement body parts.

Still further in accordance with the present invention, there are provided methods for assessing the distribution and/or structure of mitochondria in living cells by autofluorescence. In this regard, the present invention provides a method wherein fluorescence emission is measured in the region of 450 nm after excitation at 366 nm from reduced pyridine nucleotides (NADH and NADPH) located in the cytoplasm and mitochondria, with far greater quantum yield from the mitochondrial bound species than from the cytoplasmic species. The fluorescence from mitochondria as measured by this non-invasive method is useable to distinguishing different cellular states.

Still further in accordance with the present invention, there is provided a method and system for autoflorescence monitoring of living cells in a cell culture or other medium. This system generally comprises an excitation/detection fluorescence microscope apparatus, a microscopic stage and a cell growth chamber in which cells are maintained under controlled conditions (e.g., controlled temperature, humidity, pH, osmolality, nutrient levels, ion levels, ambient gas composition(s) (e.g. ambient CO2, O2 and N2), etc.) The excitation/detection fluorescence microscope apparatus is useable to continually or periodically obtain autofluorescence measurements of cells contained in the chamber. Thus, this system and method can be used to observe the natural evolution of mitochondrial organization and metabolism. Also, the cell culture may optionally be exposed to a treatment (e.g., a test compound, toxin, drug or other challenge or perturbation of a physical, chemical, thermal, metabolic, nutritional or other sort). The system and method may then be used to determine the effects of such treatment on mitochondrial organization and metabolism and/or other cellular variables measurable by autofluorescence. For example, this method and system may be used to study the effects of heating or cooling the cells, hypoxia or hyperoxia, or even the effects of different substances or drugs such as anti-cancer drugs. Time laps over minutes, hours, days and weeks may be examined.

Further aspects, objects, applications, details and variations of the present invention will be understood by those of skill in the art upon reading of the detailed description and examples set forth herebelow.

DETAILED DESCRIPTION AND EXAMPLES

The following detailed description and the accompanying drawings are intended to describe some, but not necessarily all, examples or embodiments of the invention only. This detailed description and the accompanying drawings do not limit the scope of the invention in any way.

Example 1

Redox Fluorometry Imaging as a Non-Invasive Technique for Distinguishing Mesenchymal Stem Cells (MSCs) From Further Differentiated Cells Adult bone marrow-derived mesenchymal stem cells have been demonstrated to be pluripotent for differentiation into such tissues as bone, cartilage and tendon. Standard techniques now exist to culture these stem cells in vitro for experimental study and manipulation. It has been shown that differentiation along different pathways may be controlled by media as well as substrate. Although much effort has been expended in searching for stem cell probes, currently there still exists no reliably specific marker for stem cells of any type. Additionally, many of the markers that have been proposed and studied are invasive to the cell or cell surface and may alter or even kill the cell.

One of the most accepted properties of stem cells is their ability to slowly cycle and continuously replenish cell populations. In this example, it is demonstrated that MSCs cultured in stem cell and osteogenic media have slower intrinsic metabolism than differentiated cells and, thus, may be detected by the non-invasive metabolic auto fluorescence spectroscopic technique of redox fluorometry.

Materials and Methods

A. Stem Cell and Osteogenic Media The following were used in mesenchymal stem cell growth media (Cambrex, East Rutherford N.J.): MSCBM Basal Medium (2 ml) supplemented with two vials of 25 ml fetal bovine serum (FBS) to attain an overall concentration of 10%, L-glutamine 200 mM (10 ml) and penicillin 25 U/streptomycin 25 $\mu$.g (0.5 ml) (MSCGM SingleQuots Bullet Kit, Cambrex, East Rutherford N.J.). Subcultures were performed after treatment with Trysin/EDTA 0.25 mg/ml and trypsin neutralizing solution (TNS).

Osteogenic media consisted of DMEM without sodium pyruvate (Invitrogen, Carlsbad, Calif.), 100 nM dexamethasone (Sigma Chemicals, St. Louis, Mo.), 50 M ascorbic acid-2-phosphate (Sigma), 10 mM—glycerophosphate (Sigma), 10% FBS, 100 U/mL penicillin (Invitrogen) and 100 g/mL streptomycin (Invitrogen, Carlsbad, Calif.).

B. Mesenchymal Stem Cell Harvest and Isolation Bone marrow samples from goat femurs (Thomas Morrs, Inc, Reisterstown, Md.) were washed and centrifuged (1000 rpm for 10 minutes) twice in media (Cambrex, East Rutherford N.J.) and resuspended in fresh media thereafter. Mononuclear cells were counted using a hemocytometer and were plated in culture flasks at a density of 120,000 cells/cm2. The culture media was changed after 4 days, then every 2-3 days thereafter until confluence.

C. Freezing and Thawing Cells Cells were centrifuged and the media was aspirated and replaced with an appropriate amount of freezing media: 40% MSCGM, 50% FBS and 10% dimethyl sulfoxide (DMSO). The cells were then aliquoted into cryo-vials and frozen at a controlled rate of −1° C./minute at −80° C. at a concentration of 2-3 million cells/mL. After 24 hours, the vials were transferred to liquid nitrogen for long-term storage. To thaw cells, the frozen vial was placed and gently swirled in a 370C water bath.

D. Plating and Passaging Cells After thawing, the concentrated cell solution (1-3 million cells/ml) was diluted with more media to obtain a density of 5000 cells/cm2 for plating. Media change was performed every 2 to 3 days. Upon reaching confluence (at approximately 5 days), the media was aspirated and the cells were rinsed with phosphate buffered saline solution (PBS) to prepare them for passaging. After rinsing, the PBS was aspirated and the cells were trypsinized for 5 minutes in accordance with well known standard technique. Cell release from the culture plate was confirmed under microscopic visualization and TNS was added to the solution in order to neutralize the trypsin. The solution was then placed in a centrifuge tube and spun for 10 minutes at 1000 rpm. Trypsin was aspirated and the cells were re-suspended in fresh media. The cells were counted and then were either replated for future passages or used for fluorescence imaging.

E. Autofluorescence Microscopy All images were obtained using a Zeiss (Thornwood, N.Y. inverted microscope (Axiovert 200M) with a 100× objective (FLUAR 100×, 1.3 oil). The microscope was equipped with a mercury lamp (HB 103) and a cooled CCD camera (Axiocam $MR^c5$) for taking images. To detect intrinsic reduced pyridine nucleotides, a Zeiss DAPI filter set (excitation: G365, emission: bandpass 445/50) was used. Oxidized flavoproteins were identified using a Zeiss FITC filter set (excitation: bandpass 450-490, emission bandpass 515-565). To minimize photobleaching and light stimulation, the illumination source was turned off during fluorescence imaging. All the images and fluorescence ratios were processed and analyzed using AxioVision Softare (Zeiss). Prior to auto fluorescence microscopy all cells were plated and expanded on glass surfaces (MatTek Cultureware dishes, Ashland, Mass.). Additionally, cell cultures were equilibrated in colorless PBS solution before imaging.

F. Fluorescent Dyes and Subcellular Markers To confirm the identity of auto fluorescent cellular structures, labeling dyes were used to stain the specimens. MitoTracker Green PM and LysoTracker Red (Molecular Probes, Inc., Eugene, Oreg.) were allowed to warm in room temperature and subsequently diluted with Dulbecco's Modified Eagle Medium (DMEM) to the desired concentrations, 30 nM and 75 nM respectively. Cell culture media was removed and replaced with the appropriate, pre-warmed (37° C.) probe-containing medium. Incubation was carried out for 30 minutes with MitoTracker Green FM and 1 hour for LysoTracker Red. The cells were then washed with buffer solution and imaged with the appropriate Zeiss FITC (excitation: bandpass 450-490, emission: bandpass 515-565) and Rhodamine (excitation: bandpass 546/12, emission: bandpass 515-565) filter sets.

Results

Two dimensional redox fluorometric microscope photos were of second passage goat mesenchymal stem cells (MSCs) isolated, culture expanded and examined as detailed in Materials and Methods. These redox fluorometric microscope photos demonstrated low density and higher density clustered cells, respectively, excited in the region of 366 nm and emission detected in the region of 450 nm (channel). The same cells where then excited around 460 nm and detected around 540 nm (channel 2). Unprocessed images of the previous image sets were then overlaid, with the 450 nm emission (channel 1) pseudo-colored green and the 540 nm emission (channel 2) pseudo-colored red. The PN/Fp ratios were calculated for 1) low density MSCs in stem cell media, 2) high density clustered MSCs in stem cell media, 3) low density MSCs in osteogenic media and 4) high density clustered MSCs in osteogenic media. The differences between the observed PN/Fp ratios were tested for statistical significance using the as shown in Table 1 below:

TABLE 1

Autofluoresence (PN/Fp) Ratios

| Cell Type | Pyridine (channel 1)/ Flavoprotein (channel 2) | P Value |
|---|---|---|
| 1. Low Density MSCs in stem cell media (n = 15) | 2.19 ± 0.59 | |
| 2. High Density clustered MSCs in stem cell media (n = 15) | 1.45 ± 0.27 | P = 0.0001 vs. 1 |
| 3. Low Density MSCs in osteogenic media (n = 15) | 1.38 ± 0.57 | P = 0.0007 vs. 1 |
| 4. High Density clustered MSCs in osteogenic media (n = 15) | 0.87 ± 0.34 | P = 0.00002 vs. 2 P = 0.007 vs. 3 |

This example demonstrates that redox fluorometry imaging of MSCs expanded in culture is feasible. Moreover, besides providing simple metabolic information, reasonably detailed cytoarchitecture is also visible. Based on that which was known in the prior art, it could reasonably have been predicted that nearly all of the stimulated autofluorescence observed would arise from superimposed mitochondrial compartments. However, the overlayed images showed separation of the two pseudo-colored compartments (green and red), especially in the non-clustered cell image, with less blended (yellow) overlap than expected. The reduced pyridine species stimulated at 366 nm appeared to fluoresce in a mitochondral pattern (green), whereas the oxidized flavoproteins stimulated at 460 nm appear to be comparentalized into a combination of mitochondra and lysosomes/peroxisomes (red). This was not completely unexpected, though, as a significant traction of flavin-associated autofluorescence is non-redox responsive, although most of this fluorescence is quenched when bound as protein co-factors. The remaining observed non-redox responsive fluorescence has been found to not co-localize with mitochondral sub-cellular markers, but rather with lysosomal markers. To confirm these subcellular anatomic locations, secondary staining with Mito-tracker and Lyso-tracker dyes (Molecule Probes, Inc., Eugene, Oreg.) was performed.

Results and Discussion

As expected, the pyridine/flavoprotein ratio decreased upon transitioning from the stem cell to the differentiated state. When compared to differentiated cells, the lower cellular respiration in the stem cells resulted in a higher reduced pyridine nucleotide fluorescence signal (channel 1) and a lower oxidized flavoprotein fluorescence signal (channel 2). Thus, the stem cells demonstrated a significantly higher channel 1/channel 2 ratio (i.e., the PN/Fp Ratio). Also, significant differences are noted between low density and high density clustered cell cultures.

Commitment of stem cells to separate lineages appears to be regulated by multiple cues in the local tissue environment including mechanical ones which appear to be integral to the commitment of their fate. Altering the redox state of embryonic cells through enzymes has been shown to affect transcription factors and modify gene-expression patterns to influence totipotentiality and ultimate cell lineage. Metabolism, including the parameter of redox potential, in cultured cells is also known to depend on cell density, especially mechanical cell-cell contact, and thus cell density must be considered in maintenance of cell cultures. Work comparing immortalized to non-immortalized fibroblasts demonstrated that as soon as either type of cell came into contact with one another, the total redox potential dropped. In order to compare metabolic parameters among different cell types one should take into account the density dependence of these factors, especially low density single cell vs. higher density and more confluent. Thus there is a distinct possibility that stem cells may not possess an entirely consistent redox fluorometric signature under different culture conditions and densities. If so, as metabolic rates and sub-cellular organization may change under varying conditions and it may be necessary to perform a larger number of examinations under different conditions (e.g. differing media, substrates and densities) in order to more easily separate stem cells from non-stem cells.

Although, theoretically at least, fluorescence photobleaching of intrinsic fluorophores may be a potential problem in assays of this type, reliable signals may be obtained if experimental technique is optimized, such as by maintenance of low ambient light conditions, decreased exposure times, turning off an illumination source during fluorescence imaging, using an illumination source that emits light at a wavelength that is not within the excitation or autofluorescence wavelength detection gates being employed, shielding the sample from light during at least a portion of the procedure, etc.

Example 2

Non-Invasive Mitochondrial Imaging in Live Cell Culture

In this example, autofluorescence microscopy is used to image mitochondria in live cell culture and to detect changes in the intracellular distribution and/or structure of mitochondria under varying conditions.

Materials and Methods

Limbal epithelial cells from fresh human donor tissue not suitable for transplantation (Central Florida Lions Eye and Tissue Bank, Tampa, Fla.) were cultured within 4 days of death on uncoated and coated glass surfaces [MatTek Cultureware dishes, Ashland, Mass., EpiLife Medium, Human Corneal Growth Supplement and PSA Solution (penicillin, streptomycin, and amphotericin B), Cascade Biologics, Portland, Oreg.]. Different substrate coatings (uncoated, poly-d-lysine or collagen 1) were used and cells cultured under differing $CO_2$ incubator tensions (1%, 5% and 15%). Media was changed every three days until near confluence.

MSCs were harvested from goat femurs and isolated after washing, centrifugation and suspension. The cells were plated on uncoated glass surfaces (Matek) in either mesenchymal stem cell growth media (MSGM) made up of several components [MSCBM Basal Medium, Fetal bovine serum (FBS), L-glutamine, penicillin 25 U/streptomycin, Cambrex, East Rutherford N.J.], or osteogenic media consisted of DMEM without sodium pyruvate (Invitrogen, Carlsbad, Calif.), dexamethasone (Sigma Chemicals, St. Louis, Mo.), ascorbic acid-2-phosphate (Sigma), glycerophosphate (Sigma), FBS, 100 U/mL penicillin (Invitrogen) and streptomycin (Invitrogen, Carlsbad, Calif.). Media was initially changed after 4 days, then every 2-3 days thereafter until near confluence.

Autofluorescence microscopy images were obtained using a Zeiss (Thornwood, N.Y.) inverted microscope (Axiovert 200M) with a 100× objective (FLUAR 100×, 1.3 oil). The microscope was equipped with a mercury lamp (HB 103) and a cooled CCD camera (Axiocam MRc5) for taking images. To detect intrinsic reduced pyridine nucleotides, a Zeiss DAPI filter set (excitation: G365, emission: bandpass 445/50) was used. To minimize photobleaching and light stimulation, the illumination source was turned off during fluorescence imaging. All the images were processed and analyzed using Axio-Vision Software (Zeiss). Prior to autofluorescence microscopy imaging all cells were equilibrated in balanced salt solution (BSS, Alcon, Forth Worth, Tex.), and then imaged at room temperature under room air.

Total cellular mitochondrial distribution was determined by staining with MitoTracker® Green FM (Molecular Probes, Eugene, Oreg.). A 30 nM probe solution was prepared in DMEM (GIBCO, Grand Island, N.Y.) and incubated with the culture for 30 minutes at 37° C. after samples were rinsed twice with PBS. After incubation, each sample was again rinsed with PBS and imaged with a Zeiss FITC filter set (excitation: bandpass 450-490, emission bandpass 515-565).

Intensity histograms of autofluorescence distribution were obtained using AxioVision 4.3 (Carl Zeiss, Incorporated, Thornwood, N.Y.). Line profiles were generated to plot the intensity of gray values over the course of the perpendicular axes of the cell.

Results and Discussion

Figure 1A:
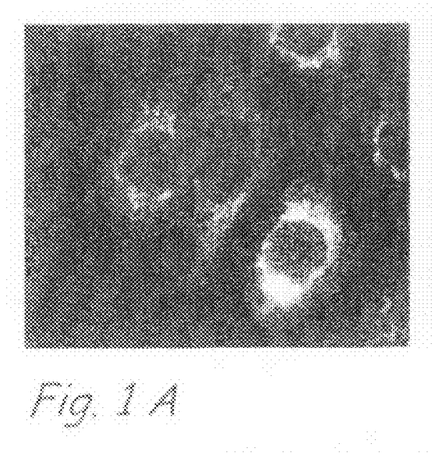
FIG. 1A is a histogram of corneal limbal epithelial cells cultured on plain glass in 1% $CO_2$.
Figure 1B:
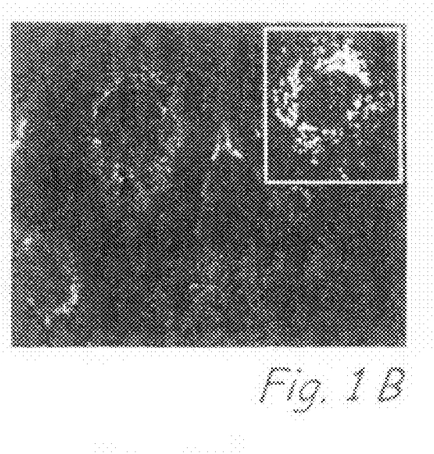
FIG. 1B is a histogram of corneal limbal epithelial cells cultured on plain glass in 5% $CO_2$. The inset in FIG. 1B shows fluorescence images of the cells of this culture stained with mitochondrial-detecting dye (MitoTracker® dye) on plain glass.
Figure 1C:
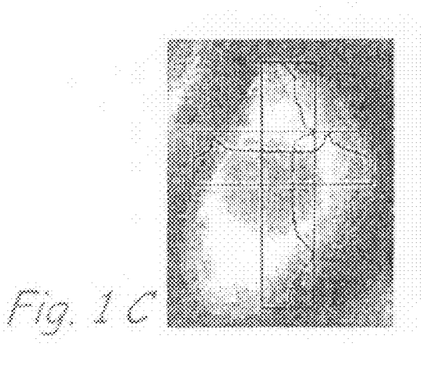
FIG. 1C is a histograms demonstrating autofluorescence distribution across cells cultured on plain glass in 1% $CO_2$.
Figure 1D:
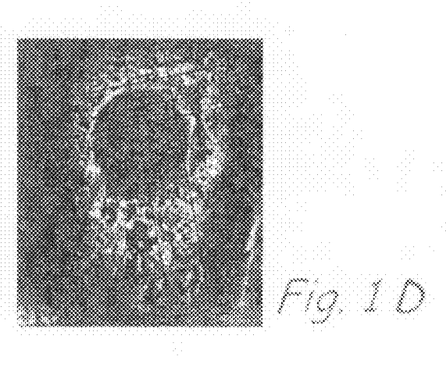
FIG. 1D is a histograms demonstrating autofluorescence distribution across cells cultured on plain glass in 5% $CO_2$.
Figure 1E:
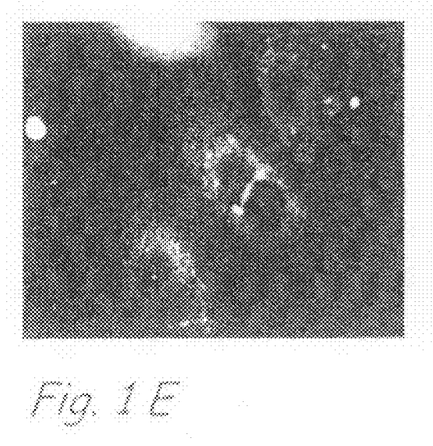
FIG. 1E is a histogram of corneal limbal epithelial cells cultured on collagen I-coated glass in 1% $CO_2$.
Figure 1F:
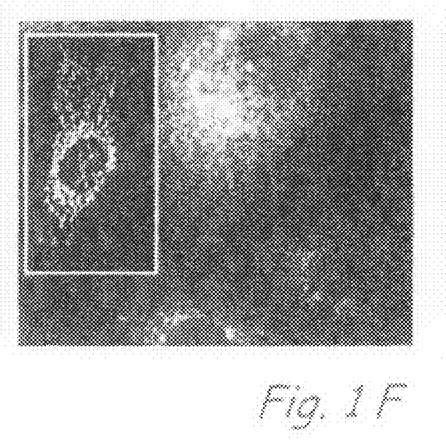
FIG. 1F is a histogram of corneal limbal epithelial cells cultured on collagen I-coated glass in 5% $CO_2$. The inset on FIG. 1F fluorescence images of the cells of this culture stained with mitochondrial-detecting dye (MitoTracker® dye).

The non-invasive mitochondrial imaging technique of the present invention was used on limbal epithelial cells grown on plain glass (FIG. 1A) or collagen I (FIG. 1E). In the 1% $CO_2$ environment, mitochondrial autofluorescence appears crowded around the nucleus. Histograms of autofluorescence distribution were obtained by measuring the intensity of gray values over the course of the perpendicular axes of the cell. The histogram in FIG. 1C demonstrates distinct peaks of autofluorescence at the nuclear border, supporting a perinuclear description. In the 5% $CO_2$ environment, as shown in FIGS. 1B and 1F, especially on the collagen 1-coated surface, in the majority of cells autofluorescence is observed to redistribute more diffusely throughout the cytoplasm where mitochondria display characteristic polymorphic structures, with spherical, tubular and bean-like shapes. A representative histogram seen in FIG. 1D has a wider distribution of broader peaks. These multiple peaks demonstrate a more diffuse distribution of autofluorescence across the ordinary and extraordinary axes of the cell.

Figure 2A:
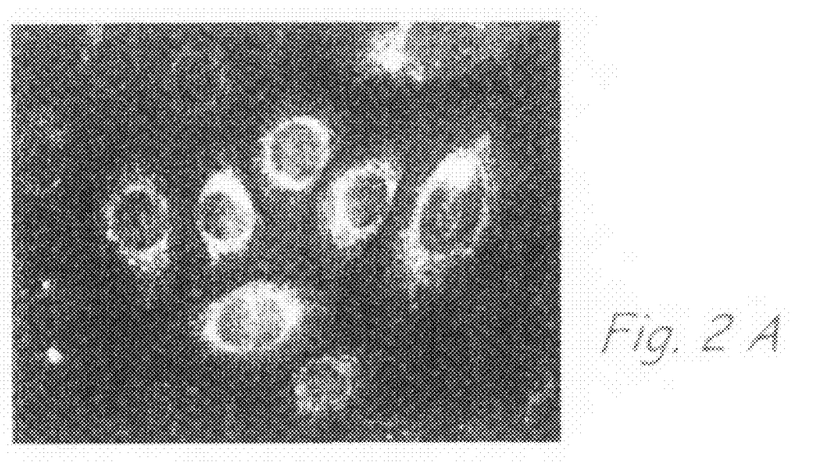
FIG. 2A is a histogram of corneal limbal epithelial cells cultured on poly-d-lysine coated plates under 1% $CO_2$.
Figure 2B:
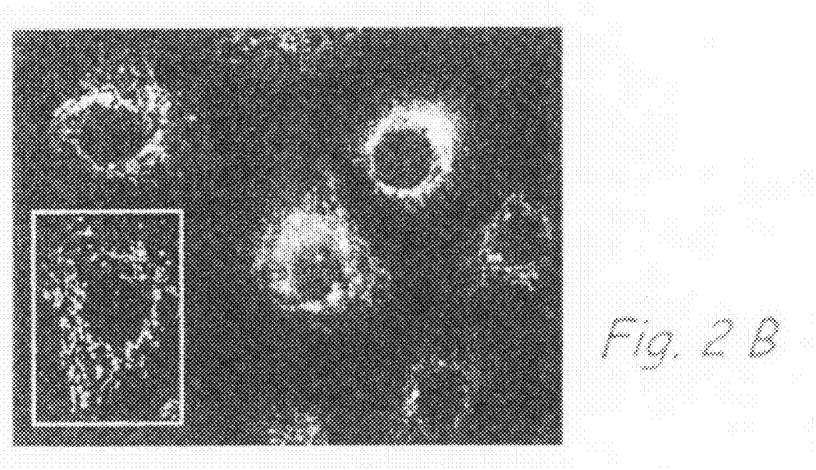
FIG. 2B is a histogram of corneal limbal epithelial cells cultured on poly-d-lysine coated plates under 5% $CO_2$.
Figure 2C:
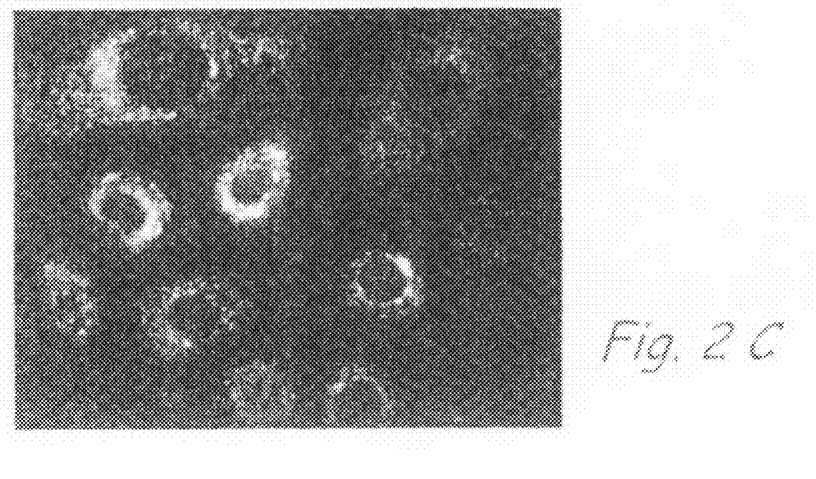
FIG. 2C is a histogram of corneal limbal epithelial cells cultured on poly-d-lysine coated plates under 15% $CO_2$. The inset in FIG. 2C shows fluorescence images of cells of this culture stained with mitochondrial-detecting dye (MitoTracker® dye).
Figure 3A:
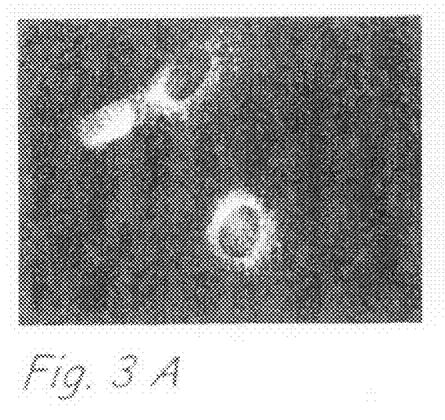
FIG. 3A is an autofluorescence images of mesenchymal stem cell cells cultured in stem cell-maintaining medium.
Figure 3B:
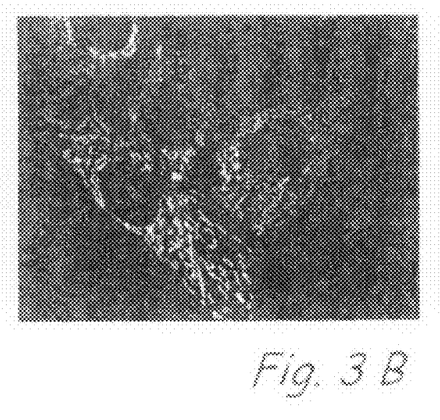
FIG. 3B shows a fluorescence image of cells of FIG. 3A later stained with mitochondrial-detecting dye (MitoTracker® dye).
Figure 3C:
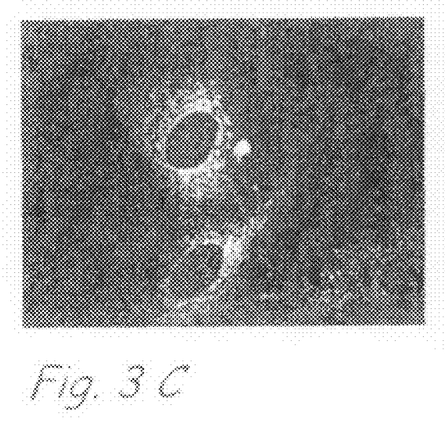
FIG. 3C is an autofluorescence image of mesenchymal stem cell cells cultured in osteogenic medium.
Figure 3D:
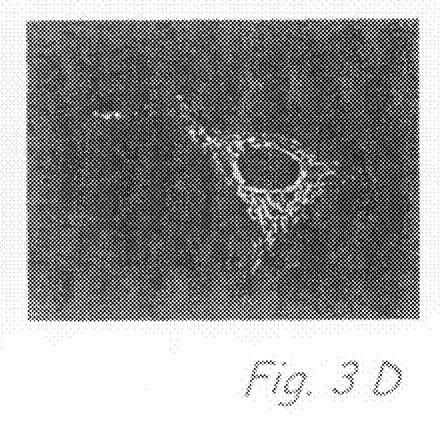
FIG. 3D shows a fluorescence image of cells of FIG. 3C later stained with mitochondrial-detecting dye (MitoTracker® dye).

FIGS. 2A-2C show autofluorescence from limbal epithelial cells expanded on poly-d-lysine-coated glass under varying $CO_2$ incubator tensions of 1% (FIG. 2A), 5% (FIG. 2B) and 15% (FIG. 2C). In cells grown in the low $CO_2$ environment (FIG. 2A), the majority of cells are observed to have higher relative mitochondrial fluorescence in the perinuclear region. In contrast, at the higher $CO_2$ concentrations (FIGS. 2B and 2C), an increasing number of larger cells are observed with structured mitochondrial fluorescence diffusing away from the perinucleus and spreading towards the cell membrane. Under all 3 environmental $CO_2$ conditions, a population of small cells appears to be resistant to the effects of the changing incubator gas mix in these heterogeneous expansions. It is possible that these small cells with marked perinuclear clustering of mitochondria belong to the stem cell pool as flow cytometry and in vivo confocal microscopy studies have demonstrated that the smallest cells in a mixed cell population originate from the limbal basal epithelium, the location of corneal epithelial stem cells.

FIG. 3 demonstrates fluorescence from MSCs grown in either stem cell maintaining (FIGS. 3A and 3B) or differentiating osteogenic (FIGS. 2C and 3D) media. Both autofluorescence in live culture (FIGS. 3A and 3C), and MitoTracker® fluorescence after fixation (FIGS. 3B and 3D) are shown. In both MitoTracker® images, it is apparent that mitochondria are actually distributed diffusely throughout the cytoplasm. In contrast, in stem cell maintaining medium unlike in osteogenic medium, there appears significant relative enhancement of autofluorescence in the perinuclear region in the majority of cells.

In this example, two techniques for imaging mitochondrial populations where compared. Traditional mitochondrial staining (MitoTracker®) is invasive and does not result in fluorescence until the stain has accumulated in the lipid environment of mitochondria. The invasive nature of this stain prohibits tracking live cells in culture serially in time. The non-invasive mitochondrial imaging methods of the present invention utilize an excitation wavelength (365 nm) away from medium and short wave UV light avoiding cellular damage and the large number of species that can autofluoresce following excitation at these short wavelengths. The major advantage of our technique is its non-invasive nature, as the cells can be imaged serially in live culture without perturbation by exogenous stains which can result in not only cell disturbance, but also death. Furthermore, because we detect metabolically active endogenous fluorophores, this also serves as a functional assay at the sub-cellular level.

Previous studies have demonstrated the co-existence of mitochondrial populations with distinct distribution patterns; diffuse mitochondria throughout the periphery of the cell and a perinuclear sequestration. The difference between these populations is the observable change in membrane potential of the active mitochondria. Each technique used in this study uses a different characteristic of the mitochondria to elucidate its distribution. The traditional MitoTracker® stain targets the lipophilic nature of the mitochondria leading to accumulation and fluoresence typically extending throughout the cytoplasm. Our autofluoresence technique relies on the metabolic activity of the mitochondria to demonstrate the sub-distribution of active mitochondria within the larger mitochondrial pool. Our findings show that mitochondrial autofluorescence distribution and appearance in living cells can change when substrates, media or ambient $CO_2$ conditions are altered.

Thus, this example demonstrates that autofluoresence imaging of mixed cell culture expansion is feasible. Additionally, reasonably detailed cytoarchitecture is visible allowing the revelation of different mitochondrial autofluorescence distribution patterns.

Figure 4:
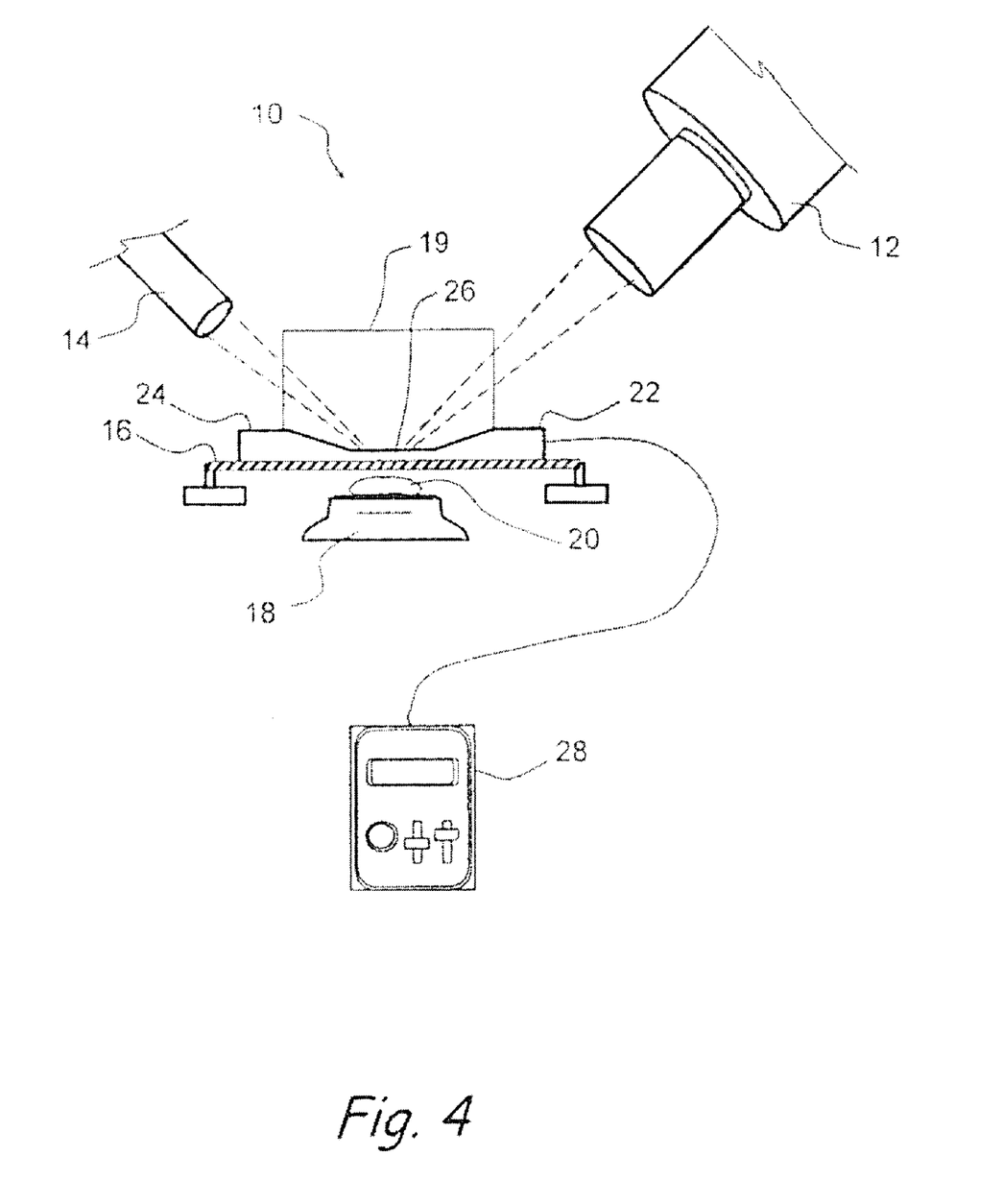
FIG. 4 is a schematic diagram of a fluorescence microscope system that incorporates a controlled condition cell culture chamber for fluorescence microscopy of living cells in accordance with the present invention.

It is to be appreciated that, in at least some embodiments, the methods of the present invention may be practiced on living cells. In the regard, the present invention includes an fluorescence microscopy system that incorporates a controlled condition cell culture chamber that enables fluorescence microscopy to be performed on living cells in culture without requiring removal of the cells from the cell culture chamber. FIG. 4 is a schematic diagram showing an example of one such fluorescence microscopy system 10 of the present invention. As shown, this system 10 comprises a focusing lens 12, an excitation light source 14, a microscope stage 16, an objective 18 having an oil droplet 20 disposed thereon, a glass cube or prism 19, a cell culture chamber 22 and a control apparatus 28 for controlling one or more conditions within the cell culture chamber 22, such as temperature, humidity, pH, osmolarity, nutrient levels, ion levels and ambient gas composition (e.g., partial pressure or concentration of $CO_2$, partial pressure or concentration of $O_2$ and partial pressure or concentration of $N_2$, etc.). Optionally, the cell culture chamber 22 may have relatively wide regions 24 located lateral to the center of the objective 18 and a thin region 26 located directly above the center of the objective 18, thereby providing a thin film of cell-containing culture medium within the thin region 26 directly above the objective 18 while allowing greater volumes of cell-containing culture medium to be present in the wide regions 24 located away from the area where the microscopic imaging occurs. Optionally, the control apparatus 28 may alternatively or additionally include a pump or motion imparting apparatus for continuously or periodically circulating cell culture medium through the portion of the culture chamber 22 located immediately above the objective (e.g., the thin region 26) thereby providing a turn-over of cells being imaged by the microscope. Also, optionally, the microscope may include a camera with a timer or other controller that causes images (e.g., histograms or other photomicrographs) of autofluorescence to be obtained at desired time points, thereby providing for observation of changes in certain parameters (e.g., mitochondrial distribution and/or structure) over a desired period of time.

Although the schematic diagram of FIG. 4 shows a fixed stage microscope, those of skill in the art will appreciate that the controlled condition cell culture chamber 22 and control apparatus 28 may also be useable in moving stage microscopes used for fluorescence microscopy.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method are described or recited in a particular order, such ordering of the steps may be changed unless doing so would render the method non-useable for its intended purpose. All reasonable additions, deletions, modifications and alterations are to be considered equivalents of the described examples and embodiments and are to be included within the scope of the following claims.

What is claimed is:

1. A method for determining whether stem cells are present in a sample that contains differentiated cells of a known cell type, said method comprising the steps of:
   (A) measuring a pyridine nucleotide to oxidized flavoprotein ratio of cells present in the sample; and
   (B) determining whether cells present in the sample exhibit a pyridine nucleotide to oxidized flavoprotein ratio that is either i) lower than that known or expected to be present in differentiated cells of the type present in the sample or ii) representative of that known or expected to be present in stem cells of a type potentially present in the sample.

2. A method according to claim 1 further comprising the step of:
   (C) counting, isolating, sorting or separating from the sample, cells that exhibit a measured pyridine nucleotide to oxidized flavoprotein ratio that is either i) lower than that known or expected to be present in differentiated cells of the type present in the sample or ii) representative of that known or expected to be present in stem cells of a type potentially present in the sample.

3. A method according to claim 1 or 2 wherein the sample comprises a cell culture medium containing cultured cells.

4. A method according to claim 1 or 2 wherein the sample comprises cells obtained from tissue harvested from a human or non-human animal.

5. A method according to claim 1 wherein the sample comprises corneal cells and the method is carried out to determine whether limbal stem cells are included in the sample.

6. A method according to claim 1 or 2 wherein the sample comprises cells obtained from umbilical chord blood.

7. A method according to claim 1 or 2 wherein the sample comprises cells obtained from bone marrow.

8. A method according to claim 1 or 2 wherein the sample comprises embryonic cells.

9. A method according to claim 1 or 2 wherein the sample comprises a solid tissue sample.

10. A method according to claim 9 wherein two-photon excited fluorescence is used to perform the method on cells located beneath the surface of the solid tissue sample.

11. A method according to claim 1 or 2 wherein Step B comprises i) selecting a minimum expected pyridine nucleotide to oxidized flavoprotein ratio for differentiated cells of the type present in the sample from a database of pyridine nucleotide to oxidized flavoprotein ratios determined for various cell types and ii) comparing the actual pyridine nucleotide to oxidized flavoprotein ratio of cells determined in Step A with the selected minimum expected pyridine nucleotide to oxidized flavoprotein ratio.

12. A method according to claim 1 or 2 wherein a pyridine nucleotide to oxidized flavoprotein ratio of cells present in the sample is measured in Step A by i) determining a first fluorescence emission value indicative of cellular components from reduced pyridine nucleotides, ii) determining a second fluorescence emission value indicative of cellular levels of the flavoproteins lipoamide dehydrogenase (LipDH) and electron transfer flavoprotein (ETF) and iii) determining the ratio of the first fluorescence emission value to the second fluorescence emission value.

13. A method according to claim 12 wherein the first fluorescence emission value is determined by measurement of fluorescence in the region of 450 nm after excitation at 366 nm.

14. A method according to claim 12 wherein the second fluorescence emission value is determined by measurement of fluorescence detected in the region of 540 nm after excitation at 460 nm.

15. A method according to claim 2 wherein Step C is carried out using a fluorescence activated cell sorter.

16. A method according to claim 1 or 2 further comprising the step of:
   decreasing exposure of the sample to light at wavelengths that will cause photobleaching.

17. A method according to claim 16 wherein the step of decreasing exposure of the sample to light at wavelengths that will cause photobleaching comprises turning off an illumination source during fluorescence imaging.

18. A method according to claim 16 wherein the step of decreasing exposure of the sample to light at wavelengths that will cause photobleaching comprises using an illumination source that emits light at a wavelength that is not within the excitation or autofluorescence wavelength detection gates being employed.

19. A method according to claim 16 wherein the step of decreasing exposure of the sample to light at wavelengths that will cause photobleaching comprises shielding the sample from light during at least a portion of the procedure.

20. A method according to claim 1 or 2 wherein the sample contains living cells.

21. A method according to claim 20 wherein the method is carried out while the sample is held in a sample containment apparatus that maintains the living cells under controlled conditions.

22. A method according to claim 21 wherein the controlled conditions include at least one condition selected from the group of: temperature, humidity, pH, osmolarity, nutrient levels, ion levels and ambient gas composition.

23. A method according to claim 21 wherein the method is repeated at one or more time points to determine changes in the cellular make-up of the sample.

24. A method according to claim 21 wherein the method is performed a first time, thereafter the living cells are contacted with at least one of test compounds, toxins, drugs, chemicals, thermal energy, metabolic agents and nutritional agents, and thereafter the method is performed a second time to determine an effect or lack of an effect based on the contacting.

* * * * *